United States Patent [19]

Chang et al.

[11] Patent Number: 4,765,969
[45] Date of Patent: Aug. 23, 1988

[54] CONTINUOUS PROCESS FOR SCRUBBING HYDROGEN SULFIDE TO PRODUCE ELEMENTAL SULFUR

[75] Inventors: Dane Chang, Houston; Michael C. McGaugh, Angleton, both of Tex.

[73] Assignee: The Dow Chemical Company, Midland, Mich.

[21] Appl. No.: 3,884

[22] Filed: Jan. 15, 1987

Related U.S. Application Data

[63] Continuation-in-part of Ser. No. 805,673, Dec. 6, 1985, abandoned.

[51] Int. Cl.$^4$ ...................... B01D 53/34; C01B 17/05
[52] U.S. Cl. ............................. 423/573 R; 423/234; 423/571
[58] Field of Search .................... 423/234, 571, 573 R

[56] References Cited

U.S. PATENT DOCUMENTS 3,536,618 10/1970 Urban et al. .................. 423/571
3,594,125 7/1971 Hamblin ...................... 423/573 R

OTHER PUBLICATIONS

Hackh's Chemical Dictionary, 4th ed. Julius Grant, McGraw-Hill Book Co. 1969, p. 40.

Primary Examiner—John Doll
Assistant Examiner—Jeffrey Edwin Russel
Attorney, Agent, or Firm—A. E. Pierce

[57] ABSTRACT

A continuous process for removing hydrogen sulfide from a gas stream by contacting the gas stream with a solution of ammonium hydroxide to produce an effluent liquid stream comprising ammonium sulfide which is fed to a heating zone maintained at least at the boiling temperature of said solution and supplied with an oxygen containing gas sparge wherein ammonia and hydrogen sulfide are removed from said zone as vapor and sulfur is removed from said zone as an aqueous dispersion, the sulfur being separated in a filtration zone from the residual aqueous liquid which is recycled back to a contact zone together with said ammonia and said hydrogen sulfide vapor.

8 Claims, 1 Drawing Sheet

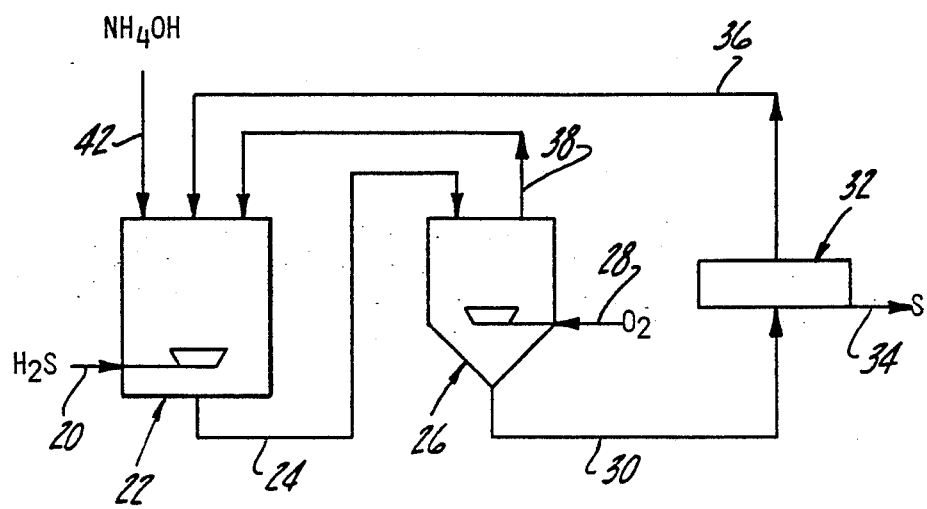

CONTINUOUS PROCESS FOR SCRUBBING HYDROGEN SULFIDE TO PRODUCE ELEMENTAL SULFUR

CROSS REFERENCE TO RELATED APPLICATION

This is a continuation-in-part of Application Ser. No. 805,673, filed Dec. 6, 1985, now abandoned.

BACKGROUND OF THE INVENTION

(1) Field of the Invention

The present invention relates generally to the removal of hydrogen sulfide from a gas stream utilizing an ammonium hydroxide aqueous solution to absorb the hydrogen sulfide and to the conversion of absorbed hydrogen sulfide to elemental sulfur and the separation of sulfur and the recycling of residual absorbed gases and aqueous liquid to the process.

(2) Description of the Prior Art

The removal of $H_2S$ from a gas stream is a problem that has long confronted and challenged workers in many diverse industries. One example is in the natural gas industry where the $H_2S$ content of certain gas streams recovered from natural gas deposits in many areas of the world is often too high for commercial acceptance. Another example is in the manufactured gas industry or the coke-making industry where coal gas containing unacceptable amounts of $H_2S$ is commonly produced by the destructive distillation of bituminous coal having a high sulfur content. Yet another example is found in the manufacture of water gas or synthesis gas where it is not unusual to produce gas stream containing $H_2S$ by passing steam over a bed of incandescent coke or coal containing a minor amount of sulfur.

More frequently, this problem is encountered in the petroleum refining industry because the principal raw material used, crude oil, typically contains a minor amount of sulfur—principally in the form of organic sulfur compounds. During the course of the many processes to which the crude oil or fractions thereof are subjected, one or more gas streams containing $H_2S$ are quite commonly produced. For example, in many cases one of the produce streams from a hydrocarbon conversion process is a gas stream containing $H_2S$ in admixture with hydrogen and/or with light, normally gaseous hydrocarbons—mainly, $C_1$-$C_3$. As is well known in the art, the presence of $H_2S$ in these refinery gas streams can cause a number of detrimental problems in subsequent processing steps such as corrosion of process equipment, deterioration and deactivation of catalysts, undesired side reactions, increase in gas compressor capacity, etc.

Regardless of the source of the gas stream containing $H_2S$, the problem of removing $H_2S$ therefrom has been solved in a number of different ways which generally involve one or more of the following techniques: selective absorption with a wide variety of absorbents, adsorption by a suitable adsorbent, selective reaction with a reagent which produces an easily separable product, etc. The details of these techniques are well known to those skilled in the art. One old and well-known solution to this $H_2S$ removal problem involves scrubbing the gas stream with an ammoniacal aqueous solution. For example, in Germany the Perox process, which uses ammonia scrubbing, has been widely used for coal gas purification. Despite the considerable amount of effort that has been devoted to developing an acceptable solution to this problem, the use of ammoniacal scrubbing has not been universally accepted in the gas treating art as the preferred method for removing $H_2S$ from a gas stream primarily because of a number of operational difficulties associated with its implementation.

One difficulty involves the relatively high partial pressure of ammonia at preferred scrubbing temperatures which generally requires that the scrubbing step be conducted with a relatively dilute ammonia solution or under relatively high pressure. The use of a dilute scrubbing solution in turn quite commonly forces the addition of a separate water wash step after the ammonia scrubbing step in order to remove ammonia from the treated gas stream. In addition, the use of dilute scrubbing solutions typically increases substantially the regeneration costs where the regeneration step is conducted at a considerably higher temperature than the scrubbing step, although some of this heat load can be recovered by a suitable heat exchanging procedure.

Another difficulty is associated with the regeneration of the rich absorbent solution withdrawn from the $H_2S$-scrubbing step. In order to minimize the requirements of the scrubbing step for water and ammonia, it is necessary to remove sulfide from this rich absorbent. Several regeneration procedures have been proposed but they typically have involved the use of absorbent-soluble catalysts such as hydroquinone and have had problems such as contamination of the sulfur product with the catalyst, excessive formation of the undesired by-products such as ammonium sulfate and thiosulfate and loss of scrubbing solution and catalyst during the periodic purges that are generally required to remove side products from the system.

Other difficulties have been associated with the recovery of the elemental sulfur from the regeneration step where in some processes it has been customary to form a froth of sulfur in the absorbent regeneration vessel which then must be skinned off and filtered. In short, it is clear that there are a significant number of technical problems associated with the prior art methods for removing $H_2S$ from a gas stream by the method of scrubbing with an ammoniacal solution.

Representative continuous processes for removing hydrogen sulfide from a gas stream are those disclosed in U.S. Pat. Nos. 3,715,426 and 3,728,440 to Hamblin. In the processes disclosed in these patents, thermodecomposition of sulfur containing anions to produce sulfur is not used. A catalytic oxidation step is used. An improved process for removing hydrogen sulfide from coke oven gases is disclosed in U.S. Pat. No. 4,342,731 and U.S. Pat. 4,518,572 to Ritter and U.S. Pat. No. 3,249,522 and U.S. Pat. No. 3,409,520 to Bolmer. In the Ritter patents, coke oven gas is washed free of hydrogen sulfide but the sulfur in the hydrogen sulfide is apparently never recovered as elemental sulfur. In the Bolmer patents, hydrogen sulfide is removed from a hydrogen sulfide-hydrocarbon gas mixture utilizing an electrolytic cell containing a porous electrode or a fuel cell containing a porous electrode. The anolyte of the cell can comprise ammonium hydroxide.

SUMMARY OF THE INVENTION

A continuous process for removal of hydrogen sulfide from a gaseous stream such as a flue gas or a gaseous hydrocarbon such as a natural gas stream comprising methane and ethane involves absorption of hydrogen sulfide in a gas-aqueous liquid contact zone with a liquid comprising ammonium hydroxide. A subsequent step involves heating an aqueous solution containing sulfur containing anions at ambient pressure in the absence of a catalyst and in the presence of an oxygen containing gas so as to produce elemental sulfur and ammonia and hydrogen sulfide vapors. The latter are recycled to the process together with the residual aqueous liquid remaining subsequent to the removal of the elemental sulfur, for instance, by filtration.

BRIEF DESCRIPTION OF THE DRAWINGS

In the FIGURE there is disclosed a continuous process for the removal of hydrogen sulfide from a gaseous stream in a contact zone 22. An aqueous liquid comprising ammonium sulfide is produced which is introduced into a heating zone 26 which an oxygen containing gas is sparging. Said liquid comprising ammonium sulfide is oxidized to elemental sulfur and ammonia and hydrogen sulfide are vaporized from the aqueous liquid for recycle to the process. Sulfur is removed from the process such as by filtration and the residual aqueous liquid remaining thereafter is recycled to the process.

DETAILED DESCRIPTION OF THE INVENTION

A process is disclosed for the removal of hydrogen sulfide and the recovery of elemental sulfur from a gas stream containing hydrogen sulfide by passing the gaseous stream containing hydrogen sulfide through a contact zone, preferably by countercurrently contacting said gaseous stream with an aqueous ammonium hydroxide solution so as to form therein sulfide and other sulfur-containing anions. The solution of sulfur containing anions and ammonium hydroxide is thereafter passed to a heating zone maintained at about the boiling point at ambient pressure of said aqueous liquid into which an oxygen containing gas such as air or oxygen is sparging. Ammonia and hydrogen sulfide are vaporized from said aqueous liquid and sulfur-containing anions are converted to elemental sulfur. Sulfur is removed from said liquid, for instance, in a filtration zone and thereafter the residual aqueous liquid together with ammonia and hydrogen sulfide is recycled to the process.

Referring now to the Figure showing in schematic form one embodiment of the invention, a gaseous mixture containing hydrogen sulfide enters the contact zone 22 through line 20. An aqueous solution of ammonium hydroxide is received through line 42 passing countercurrently in said contact zone 22 to the flow of the hydrogen sulfide gas. Upon contacting the aqueous ammonium hydroxide solution, the hydrogen sulfide is converted to a reaction product of ammonium hydroxide and hydrogen sulfide comprising ammonium sulfide and one or more other species of sulfur-containing anions. Said solution is passed through line 24 to heating zone 26 which is supplied with an oxygen containing gas through line 28. Said heating zone 26 is maintained at about the boiling point of said solution. Said sulfur-containing anions are oxidized to elemental sulfur and hydrogen sulfide and ammonia are vaporized and pass through line 38 back to contact zone 22. Subsequent to oxidation of the sulfur-containing anions in heating zone 26, an aqueous dispersion of elemental sulfur is formed which is passed through line 30 to filtration zone 32 where elemental sulfur is removed from the process through line 34 and the residual water remaining passes through line 36 back to contact zone 22.

In the process of the invention, hydrogen sulfide, contained in a hydrogen sulfide containing gas, is absorbed from the gas phase to form sulfur-containing anions by contact in a contact zone maintained at a temperature generally of about 20° to about 70° centigrade and preferably about 30° to about 50° centigrade with the aqueous ammonium hydroxide solution at a concentration of about 0.5 molar to about 1 molar so as to maintain a pH of about 8 to about 10, preferably about 9 to about 10, and most preferably about 9. The major anion component which is formed is the sulfide ion although other sulfur-containing anions such as sulfate, sulfite, bisulfate, bisulfite, thiosulfate, and polysulfide ions are formed in varying amounts.

The following example illustrates the various aspects of the invention but is not intended to limit its scope. Where not otherwise specified throughout this specification and claims, temperatures are given in degrees centigrade, and parts, percentages, and proportions are by weight.

EXAMPLE

To illustrate the process of the invention, a continuous process is performed on a laboratory scale utilizing one liter of a one molar ammonium hydroxide solution which is fed to a primary contact zone countercurrently to the flow of hydrogen sulfide gas (100%) which is introduced to the primary contact zone at a rate of 0.45 cubic feet per hour through a sparging tube. The ammonium hydroxide solution is saturated with hydrogen sulfide for a period of two hours or until the color of the solution turns yellowish-green. The solution containing as a major component the sulfide anion is then pumped at a rate of 2 to 5 milliliters per minute through a heating zone maintained at the boiling point at ambient pressure of the aqueous solution introduced therein. The temperature maintained is 95° centigrade. Evaporation of ammonia and hydrogen sulfide occurs under these conditions.

During the heating process in the heating zone, a stream of air is sparged inside the heater at a rate of 3 cubic feet per hour. The sparging stream of air increases the rate of oxidation of the sulfur-containing anions in the aqueous solution therein and increases the evolution of ammonia and hydrogen sulfide from the aqueous solution. These latter gases are recycled back to the primary contact zone. The elemental sulfur formed in the heating zone is passed to a filtration zone and removed by filtration from the process. The residual aqueous liquid is recycled back to the primary contact zone. Alternatively, the aqueous liquid from the filtration zone and the ammonia and hydrogen sulfide gases from the heating zone are recycled back to a secondary contact zone where the ammonia upon contact with water in said secondary heating zone forms ammonium hydroxide which is in turn recycled back to the primary contact zone.

While this invention has been described with reference to certain specific embodiments, it will be recognized by those skilled in the art that many variations are possible without departing from the scope and spirit of the invention, and it will be understood that it is intended to cover all changes and modifications of the invention disclosed herein for the purposes of illustration which do not constitute departures from the spirit and scope of the invention.

The embodiments of the invention in which an exclusive property or priviledge is claimed are defined as follows:

1. A continuous process for treating a gas stream containing hydrogen sulfide to produce elemental sulfur therefrom, said process consisting of:
    (A) introducing said gas stream into a gas-aqueous liquid contact zone maintained at a pH of about 8 to about 10, wherein said liquid comprises ammonium hydroxide, to produce an aqueous solution comprising ammonium sulfide as a major component;
    (B) passing said aqueous solution to a heating zone maintained at about the boiling temperature of said aqueous solution at ambient pressure, and into which there is sparged an oxygen containing gas;
    (C) heating said aqueous solution in said heating zone
        (1) to release ammonia and hydrogen sulfide from said aqueous solution and
        (2) to oxidize said aqueous solution comprising ammonium sulfide to form an aqueous dispersion of elemental sulfur;
    (D) recycling said ammonia and said hydrogen sulfide to said contact zone; and
    (E) separating sulfur from said aqueous dispersion and recycling the residual aqueous solution substantially free of sulfur to said contact zone; wherein ammonium hydroxide is formed in said contact zone upon contact of said ammonia with said aqueous solution.

2. The process of claim 1 wherein said contact zone is maintained at ambient pressure and a temperature of about 20° to about 70° centigrade.

3. The process of claim 2 wherein said oxygen containing gas is air.

4. The process of claim 2 wherein said oxygen containing gas is oxygen.

5. The process of claim 3 wherein the concentration of said ammonium hydroxide in said aqueous solution in said contact zone is about 0.5 molar to about 1 molar.

6. The process of claim 5 wherein said gas stream containing hydrogen sulfide is a flue gas or a gaseous hydrogen mixture with hydrogen sulfide.

7. The process of claim 6 wherein said gas stream is a natural gas stream.

8. The process of claim 7 wherein said natural gas is comprised predominantly of methane and ethane.

* * * * *

UNITED STATES PATENT AND TRADEMARK OFFICE
CERTIFICATE OF CORRECTION

PATENT NO. : 4,765,969
DATED : August 23, 1988
INVENTOR(S) : Dane Chang and Michael C. McGaugh It is certified that error appears in the above-identified patent and that said Letters Patent is hereby corrected as shown below:

Col. 2, line 40; "skinned off" should read --skimmed off--

Col. 3, line 18; "zone 26 which" should read --zone 26 into which--

Col. 5, line 2; "or priviledge" should read --or privilege--

Col. 6, line 19; "hydrogen mixture" should read --hydrocarbon mixture--

Signed and Sealed this

Twenty-eighth Day of February, 1989

Attest:

DONALD J. QUIGG

Attesting Officer     Commissioner of Patents and Trademarks